(12) United States Patent
Rutan et al.

(10) Patent No.: US 11,584,584 B2
(45) Date of Patent: Feb. 21, 2023

(54) CONTAINER FOR STORING AND DISPENSING RESPIRATORY MASK LINERS

(71) Applicant: Naturs Design, Inc., Jackson, MI (US)

(72) Inventors: Robert M. Rutan, Jackson, MI (US); Patrick Auell, Morrison, CO (US)

(73) Assignee: Naturs Design, Inc., Jackson, MI (US)

( * ) Notice: Subject to any disclaimer, the term of this patent is extended or adjusted under 35 U.S.C. 154(b) by 771 days.

(21) Appl. No.: 16/600,860

(22) Filed: Oct. 14, 2019

(65) Prior Publication Data

US 2020/0115143 A1 Apr. 16, 2020

Related U.S. Application Data

(60) Provisional application No. 62/745,413, filed on Oct. 14, 2018.

(51) Int. Cl.
*B65D 83/08* (2006.01)
*A61M 16/06* (2006.01)

(52) U.S. Cl.
CPC ..... *B65D 83/0805* (2013.01); *A61M 16/0605* (2014.02); *A61M 2205/0238* (2013.01)

(58) Field of Classification Search
CPC ............ B65D 83/0805; B65D 83/0894; B65D 43/161; B65D 83/08; A47K 2010/3266; A47K 2010/3233; A47K 10/32; A47K 10/421
USPC ......................................... 206/581, 494, 440
See application file for complete search history.

(56) References Cited

U.S. PATENT DOCUMENTS

| 5,615,767 | A | * | 4/1997 | Eull | ....................... B65D 85/18 206/499 |
| 5,881,877 | A | * | 3/1999 | Adams | ................... B25H 3/022 220/555 |
| 8,365,733 | B2 | | 2/2013 | Rutan | |
| 9,113,667 | B2 | | 8/2015 | Rutan | |
| 10,071,216 | B2 | | 9/2018 | Rutan | |
| 2010/0206896 | A1 | * | 8/2010 | Ray | .................... A47K 10/3818 221/45 |
| 2019/0001093 | A1 | | 1/2019 | Rutan | |

* cited by examiner

*Primary Examiner* — King M Chu
(74) *Attorney, Agent, or Firm* — Brooks Kushman P.C.

(57) ABSTRACT

A container for storing and dispensing respiratory mask liners includes a housing defining a cavity therein and a cover arranged to be received on the housing, the cover including an upper face having an opening formed therein. The container further includes a lever having a first end and a second end, the lever first end pivotally connected to the cover for engaging and dispensing respiratory mask liners stored within the container through the opening.

19 Claims, 6 Drawing Sheets

CONTAINER FOR STORING AND DISPENSING RESPIRATORY MASK LINERS

CROSS-REFERENCE TO RELATED APPLICATIONS

This application claims the benefit of U.S. provisional application Ser. No. 62/745,413 filed Oct. 14, 2018, the disclosure of which is hereby incorporated in its entirety by reference herein.

TECHNICAL FIELD

Embodiments relate to a container for storing and dispensing respiratory mask liners.

BACKGROUND

Obstructive sleep apnea is a serious and potentially fatal medical condition in which a person's airway becomes physically blocked multiple times during sleep, restricting oxygen intake and causing the person to awake gasping for breath. Possible effects of the condition include extreme fatigue, high blood pressure, strokes, heart attacks, and sometimes even death.

One of the most common treatments of obstructive sleep apnea is the use of a continuous positive airway pressure (CPAP) machine. These machines deliver a continuous flow of pressurized air to the airway through a hose and mask fitted to the face. Patient compliance is a major problem with CPAP users, however, due to discomfort, air leaks, and general ineffectiveness. It is estimated that up to 50% of users discontinue use.

Most CPAP masks currently available are made from silicone, rubber, vinyl, or a nylon-based fabric. These materials are typically water and gas impermeable, which can block off pores, cause sweating, and create pressure marks on the face, increasing the discomfort of the mask. Furthermore, most mask manufacturers recommend against the use of skin or face cream with CPAP masks since the mask material directly contacts the skin. This is a problem for many users, especially those that have dry skin and depend on night cream for skin care.

A liner can be used to improve the comfort, effectiveness, and/or patient compliance of CPAP and other respiratory masks, such as is disclosed in U.S. Pat. No. 8,365,733, incorporated by reference herein in its entirety. Such a liner may be held in place by the pressure of the respiratory mask upon the face (e.g., by straps around the head), and then the liner is easily removable and replaceable when the mask is removed. Users may purchase packs containing multiple replacement liners which must be stored and then are dispensed as needed when it is necessary for the liner currently in use to be replaced.

SUMMARY

In one or more embodiments, a container for storing and dispensing respiratory mask liners includes a housing defining a cavity therein and a cover arranged to be received on the housing, the cover including an upper face having an opening formed therein. The container further includes a lever having a first end and a second end, the lever first end pivotally connected to the cover for engaging and dispensing respiratory mask liners stored within the container through the opening.

In one or more embodiments, a container for storing and dispensing respiratory mask liners includes a housing having a generally planar base and sidewalls extending upwardly from the base. The container further includes a cover having an upper face and a rim surrounding the upper face, where the rim is arranged to be received on the sidewalls of the housing to secure the cover to the housing. The upper face has an opening formed therein, where the cover includes recessed tracks formed in opposing sides of the opening. The container further includes a lever having a first end and a second end, the lever first end pivotally connected to the tracks, the lever second end including an engagement member for temporarily adhering to and dispensing respiratory mask liners stored within the container through the opening.

In one or more embodiments, a container for storing and dispensing respiratory mask liners includes a housing having a generally planar base and sidewalls extending upwardly from the base. The container further includes a cover having an upper face and a rim surrounding the upper face, where the rim is arranged to be received on the sidewalls of the housing to secure the cover to the housing. The upper face has an opening formed therein, where the cover includes recessed tracks formed in opposing sides of the opening. A lid is pivotally connected to the cover and arranged to cover the opening. The container further includes a lever having a first end and a second end, the lever first end pivotally and slidably connected to the tracks such that the lever is movable along the tracks to a desired position with respect to the opening, the lever second end including an engagement member for temporarily adhering to respiratory mask liners stored within the container and dispensing respiratory mask liners through the opening when the lever is rotated away from the opening.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
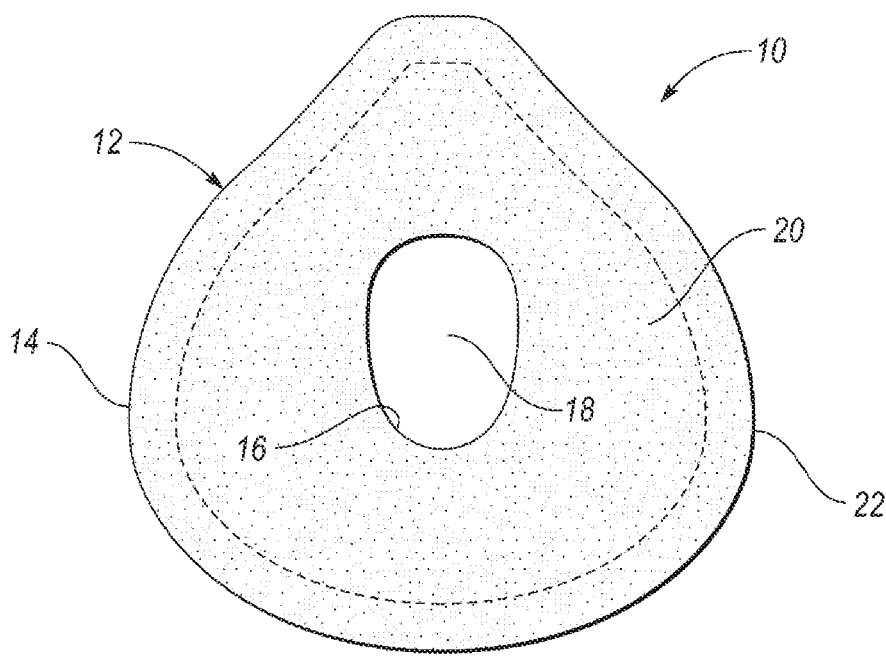
FIG. 1 is a top view of an example of a liner for use with a respiratory mask.

With reference to FIG. 1, a liner for use with a respiratory mask, such as a CPAP mask, is illustrated and designated generally by reference numeral 10, wherein this liner is disclosed in U.S. Pat. No. 8,365,733, incorporated by reference herein in its entirety. In use, the liner 10 may be positioned between and held in place by the respiratory mask and the face of a user, and may be used, for example, to absorb moisture, maintain proper positioning of the mask, and greatly reduce or eliminate air from leaking between the mask and the user's face. The liner 10 may also be used with other types of respiratory masks such as, but not limited to, oxygen masks, respirators, and filtering masks.

In one embodiment, the liner 10 includes a body 12 having an outer edge 14, an inner edge 16, and an opening 18 bounded by the inner edge 16. The body 12 may be generally oval-shaped, elliptical, round, or triangular, or have any other shape appropriate for use with a respiratory mask, and is not limited to the shape depicted herein. The opening 18 is configured to at least partially receive the nose, mouth, or both nose and mouth, depending upon the type of mask, allowing air flow from an air source to be received by the user through the mask. The opening 18 may be generally elliptical or oval-shaped as shown, but is not intended to be limited to these shapes.

According to an embodiment, the body 12 may be constructed from a single layer of absorbent material, wherein the thickness of the body 12 may be between about 0.005 to 0.05 inches, although these dimensions are not intended to be limiting. In one embodiment, the material may include cotton. In another embodiment, the material may include another material, such as silicone, with cotton embedded therein. However, it is understood that any material with suitable absorption and comfort properties may be used. In further accordance with an embodiment, the material used for the construction of the body 12 may be stretchable to aid in adjusting and customizing the fit of the liner 10 to a particular user. The absorbent material may function to absorb moisture and/or oils from the user's skin and enable the mask to maintain a consistent and comfortable position with respect to the user's face when in use.

Figure 2:
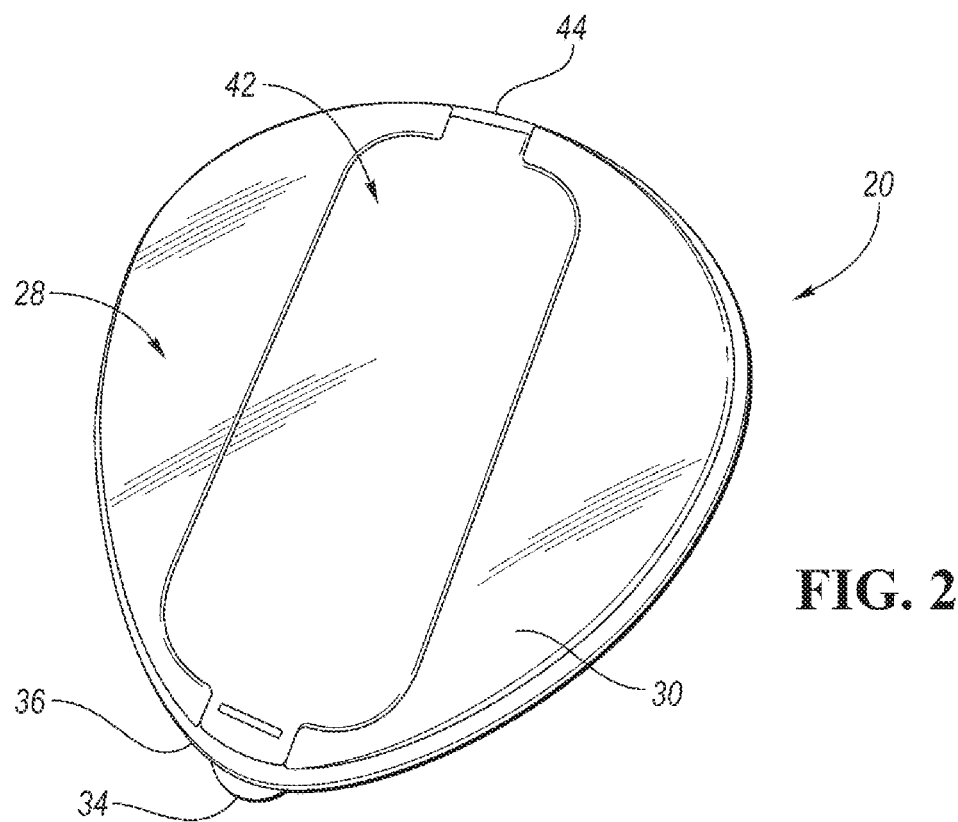
FIG. 2 is a perspective view of a container for storing and dispensing respiratory mask liners according to an embodiment.
Figure 3:
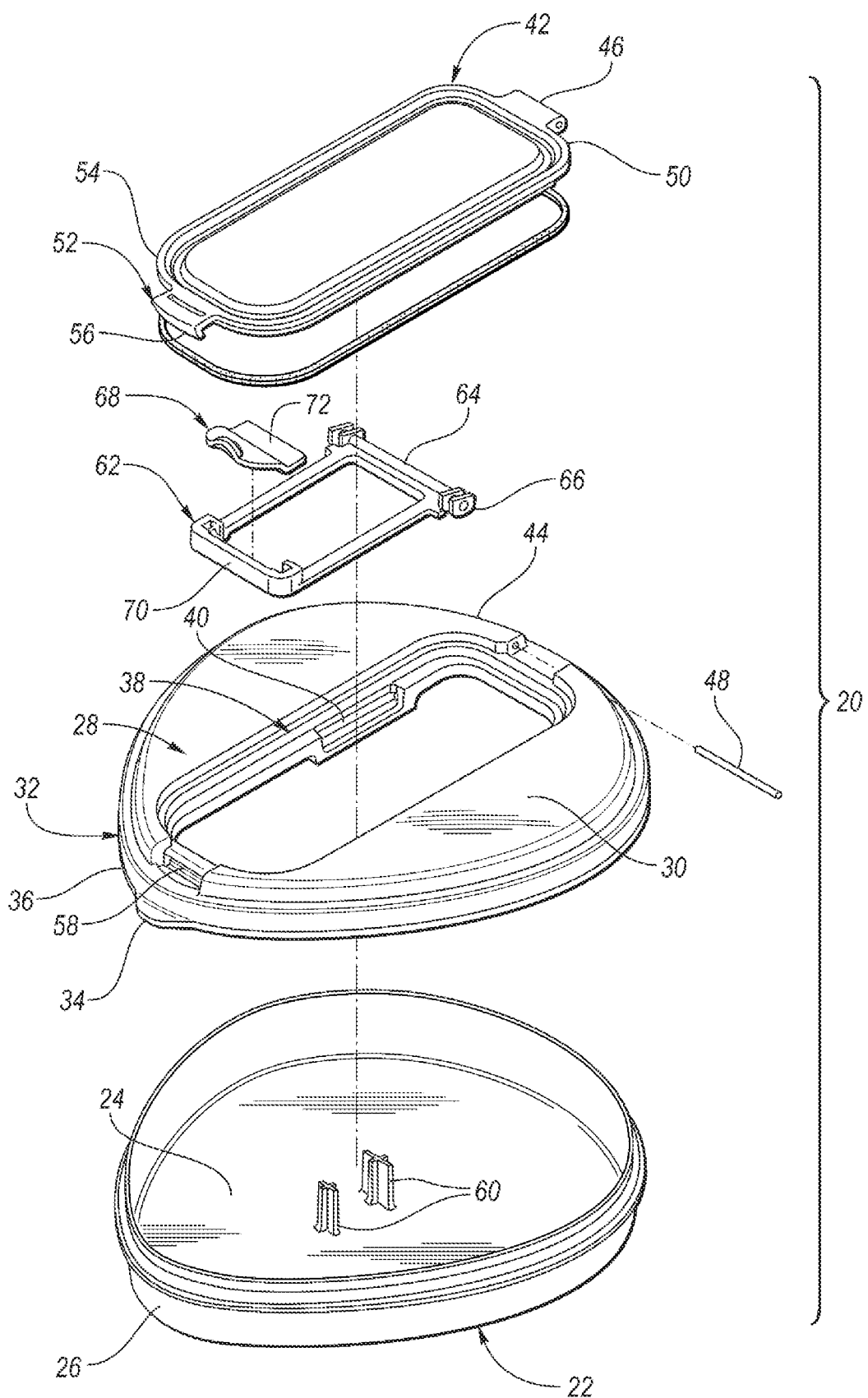
FIG. 3 is an exploded view of the container.

Turning to FIGS. 2 and 3, in one or more embodiments a container 20 is provided for storing and dispensing respiratory mask liners such as, but not limited to, liner 10. The container 20 includes a housing 22 having a generally planar base 24 and sidewalls 26 extending upwardly from the base 24, defining a cavity for receiving and storing respiratory mask liners therein. The container 20 further includes a cover 28 having an upper face 30 and a rim 32 surrounding the upper face 30 and depending downwardly therefrom. The rim 32 may be received on the sidewalls 26 of the housing 22 to secure the cover 28 to the housing 22, such as by a press-fit or a snap-fit arrangement. The cover 28 may include a tab 34 extending outwardly from a front end 36 of the cover 28 to facilitate removing the cover 28 from the housing 22, such as when filling the container 20 with liners 10 for storage. The container 20 may generally have an oval shape to correspond with the shape of respiratory mask liners 10, but the container 20 is not limited to this shape. The container 20 can be constructed from plastic or another suitable material.

An opening 38 is formed in the cover 28 and may be generally centrally disposed within the cover 28. In one embodiment, the opening 38 is generally rectangular, but is not limited to this configuration. Recessed tracks 40 are formed in the cover 28 on opposing sides of the opening 38. A lid 42 may be pivotally connected to the cover 28 at a rear end 44 of the cover 28, such as via a hinge member 46 and pin 48 at a first end 50 of the lid 42. The lid 42 is sized to correspond to the shape of the opening 38. In one embodiment, the lid 42 is received within the opening 38 so as to be flush with the cover 28 when the lid 42 is in a closed configuration (see FIG. 2). The lid 42 may also include a grip member 52 at a second end 54 of the lid 42, where the grip member 52 may include a latch portion 56 that can be received in an aperture 58 formed in the cover 28 to secure the lid 42 to the cover 28 in the closed configuration.

Respiratory masks, more particularly CPAP masks, are offered in various shapes and sizes, including full-face, nasal, child-sized, and partial-face (hybrid) configurations. Full-face masks typically include a wider bottom region for covering the mouth area and a narrower upper region for covering the nasal area. Nasal masks generally cover the nasal area and not the mouth area. Child-sized masks may have a proportionally smaller size. Partial-face (hybrid) masks generally cover the mouth and may include a nasal interface. As such, the liners 10 and their outer edges 14 and openings 18 thereof may have different shapes to corresponding to the selected respiratory mask with which they are used.

Figure 5:
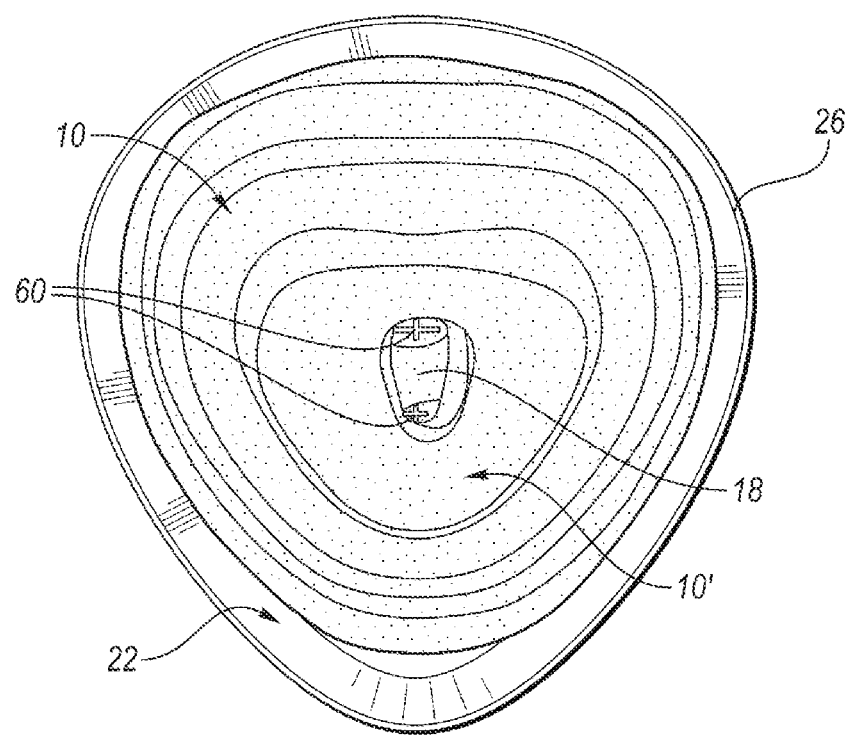
FIG. 5 is a top view of the container with the cover removed and respiratory mask liners disposed in the housing.

In order to store respiratory mask liners 10 of the same or varying sizes, the container 20 may include one or more posts 60 extending upwardly from the base 24 which may be received in the opening 18 of each liner 10, as best shown in FIG. 5. The posts 60 keep a stack of liners 10 organized and aligned, and prevent unwanted shifting of the liners 10 within the container 20.

With reference to FIGS. 3-4 and 6-7, a lever 62 may be connected to the cover 28 for dispensing respiratory mask liners 10 stored within the container 20. The lever 62 includes a first end 64 which is received by the tracks 40 of the cover opening 38. The first end 64 may include a spring 66 which is biased outwardly to engage the tracks 40, providing a pivotal engagement between the lever first end 62 and the cover 28. The lever 62 can be moved along the tracks 40 into a desired position corresponding to a size and shape of a specific liner 10 to be dispensed, as described further below.

Figure 6:
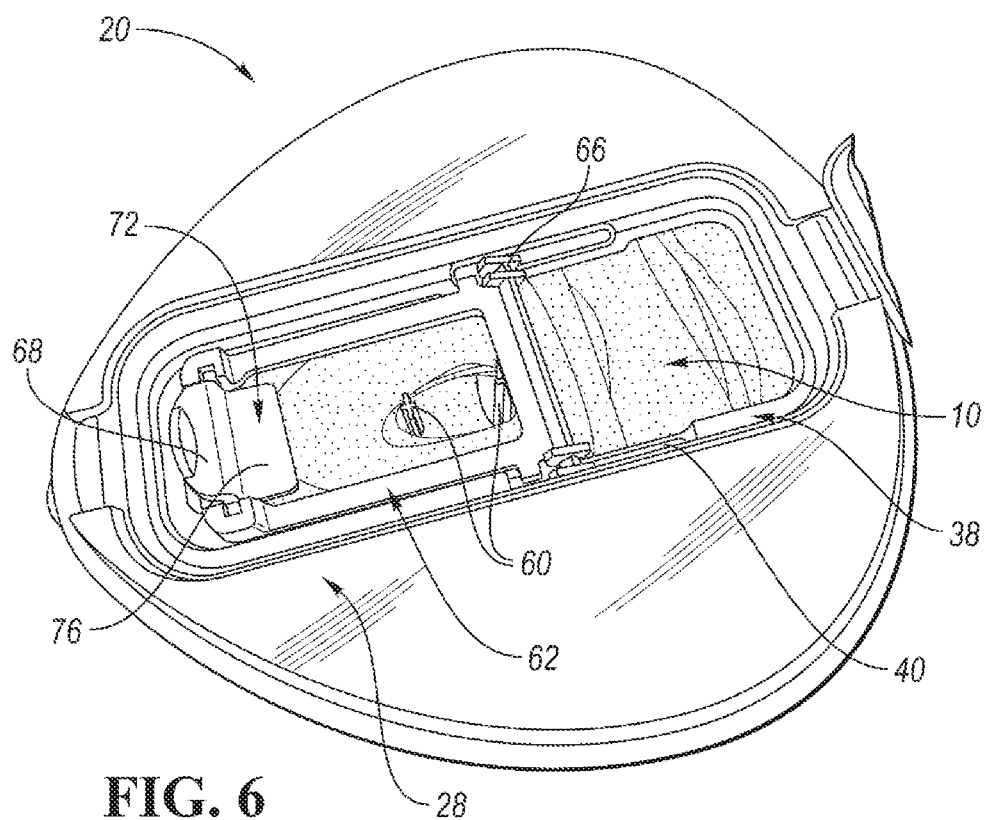
FIG. 6 is a top view of the container showing the lever in a closed configuration at a first position along a track in the cover.
Figure 7:
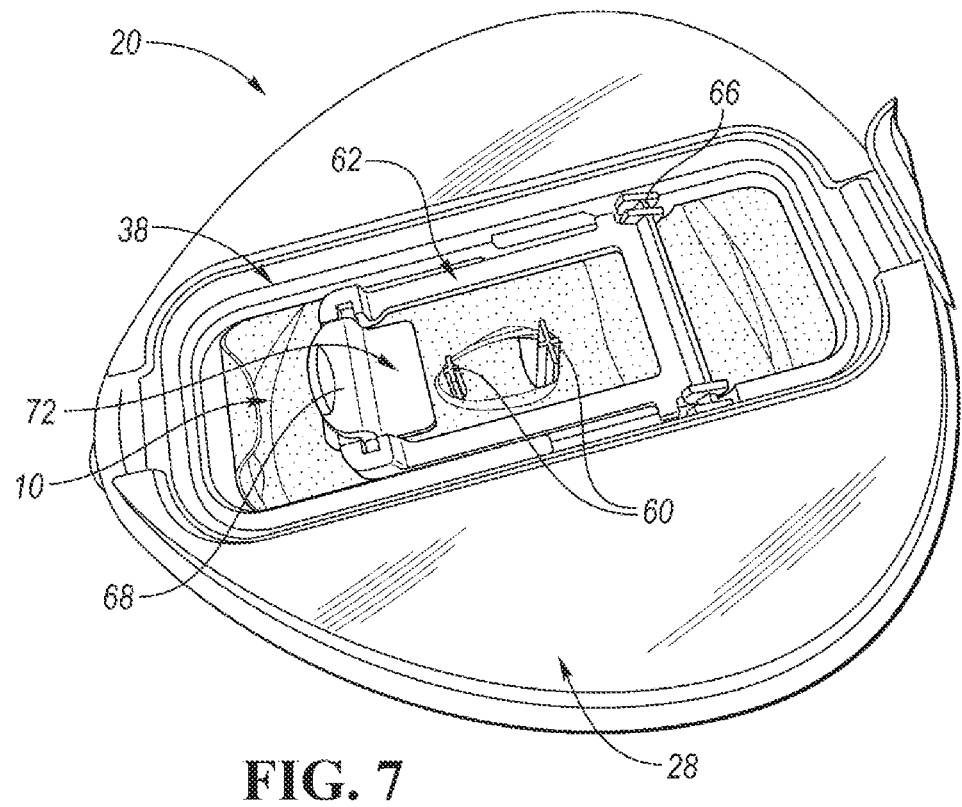
FIG. 7 is a top view of the container showing the lever in a closed configuration at a second position along the track.
Figure 8:
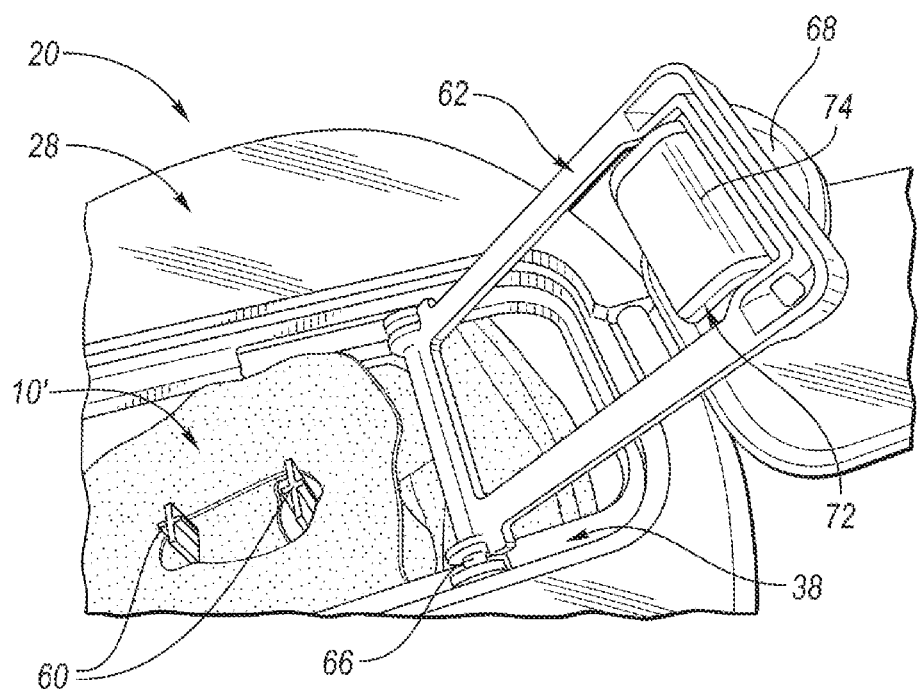
FIG. 8 is a top perspective view of the container showing the lever in an open configuration.

As shown in FIGS. 6 and 7, a handle 68 is provided at a second end 70 of the lever 62 and can be used to grip the lever 62 and pivot the lever 62 about its first end 64. An engagement member 72 is formed at the lever second end 70 for contacting and temporarily adhering to the top liner 10' stored in the container 20. The engagement member 72 may be generally planar or rounded and may comprise, for example, an adhesive or a textured bottom surface 74 (see FIG. 8) to engage and removably grip the liner 10.

Figure 4:
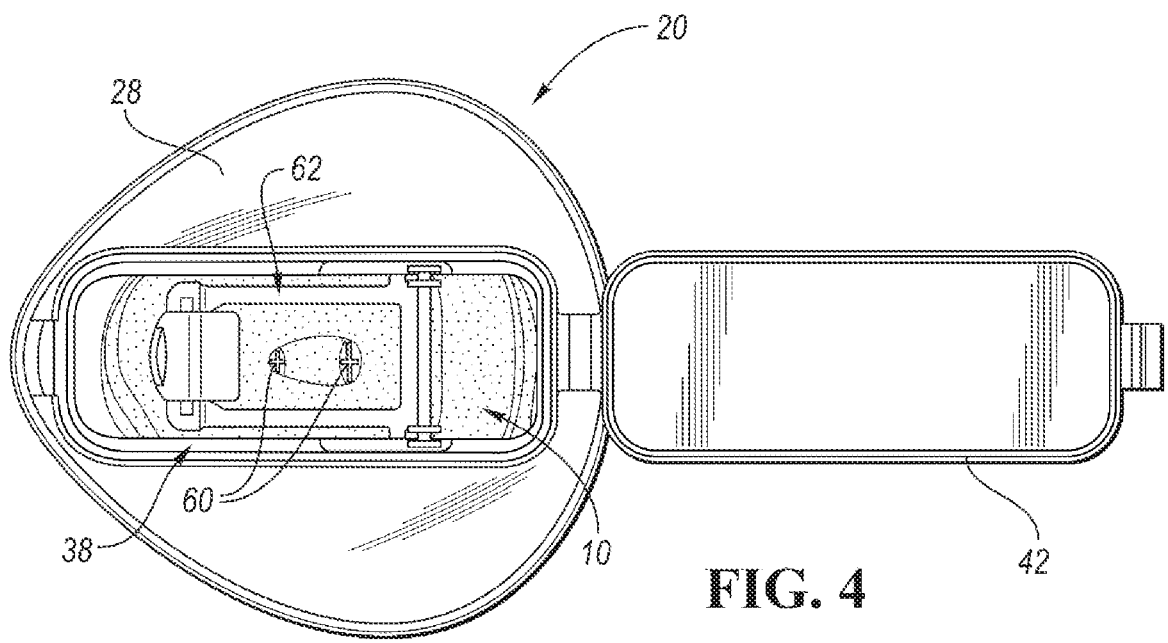
FIG. 4 is a top view of the container with the lid in an open configuration.
Figure 9:
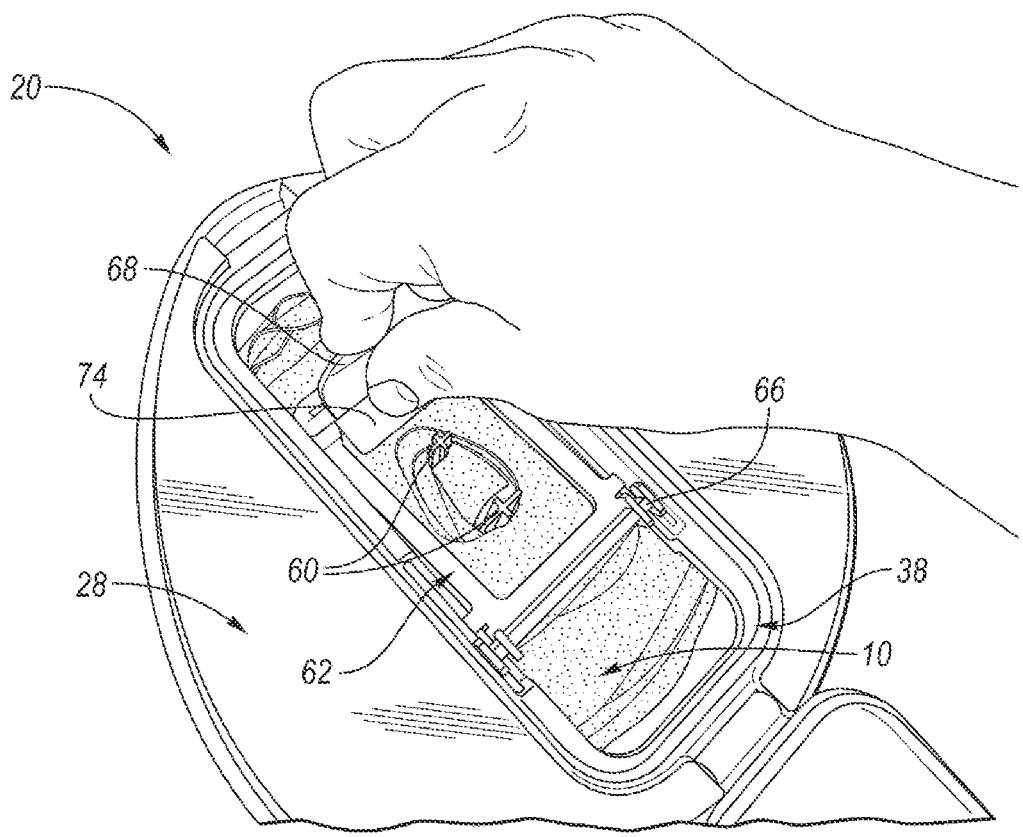
FIG. 9 is a top perspective view of the container showing the lever in a closed configuration and engaging a top liner within the housing.
Figure 10:
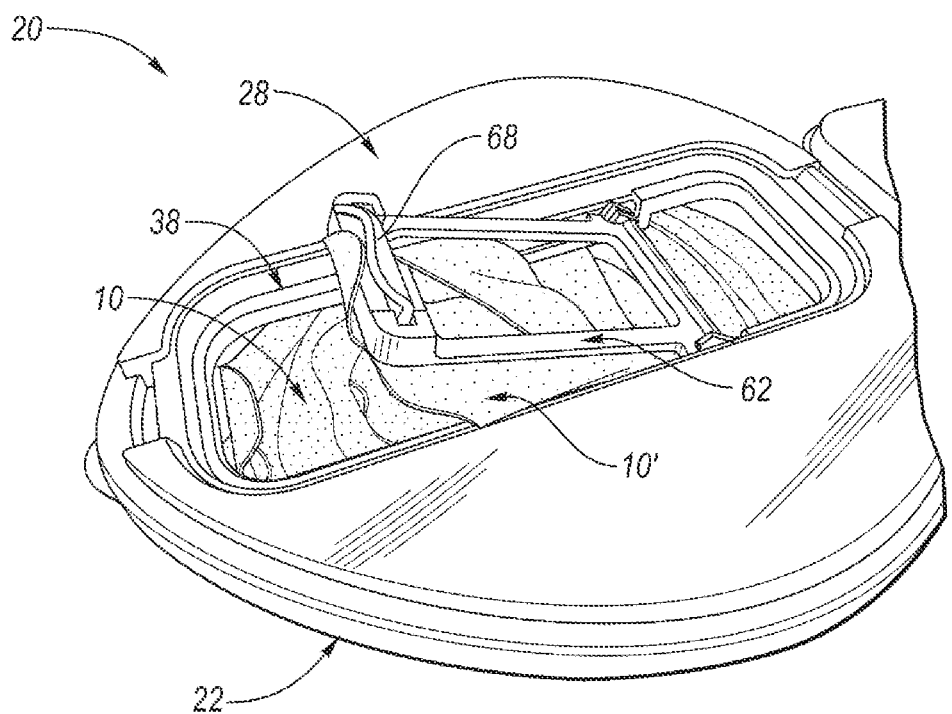
FIG. 10 is a perspective view of the container showing the lever in an intermediate configuration after engagement with the top liner.
Figure 11:
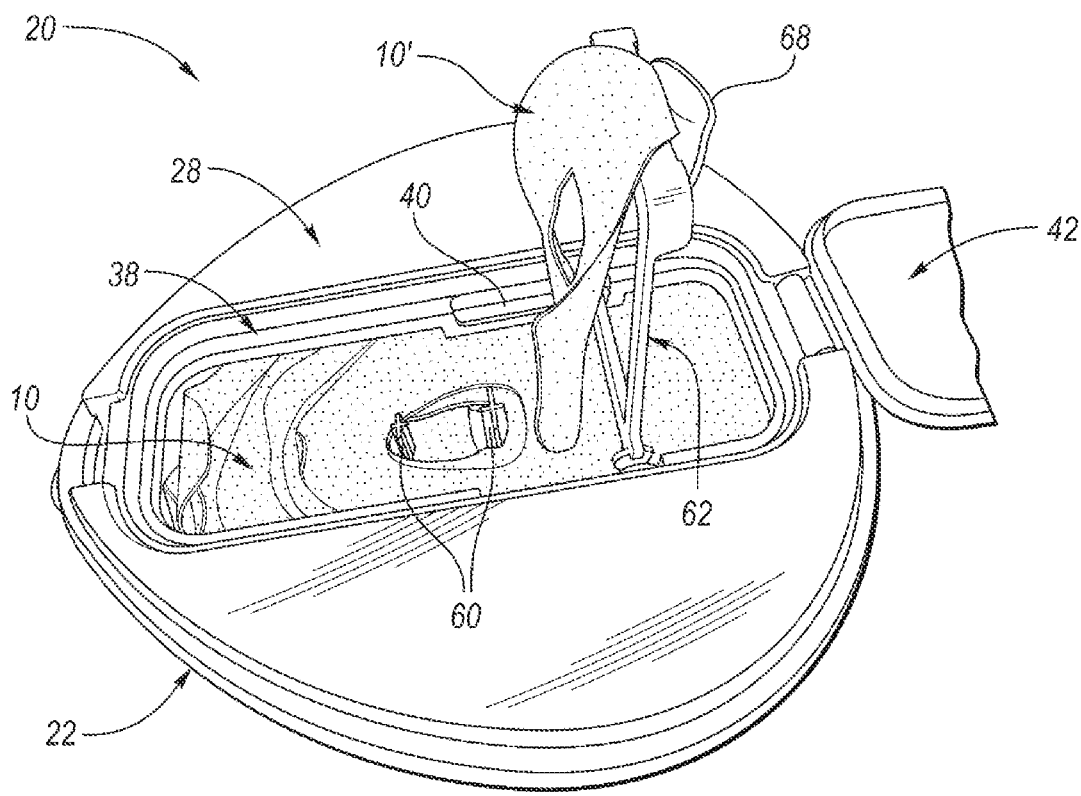
FIG. 11 is a perspective view of the container showing the lever in an open configuration with the top liner engaged.

In order to dispense a liner 10 from the container 20, a user can open the lid 42 by grasping the grip member 52 and pivoting the lid 42 to an open configuration, as shown in FIG. 4. The user may then slide the lever 62 along the tracks 40 to align the lever second end 70 with a portion of the top liner 10' within the container 20. By pressing down on a top surface 76 of the engagement member 72 (which may be accomplished by either direct pressure on the top surface 76 or via downward pressure on the handle 68) the bottom surface 74 contacts the liner 10, as illustrated in FIG. 9. The user can then pull back on the handle 68 to rotate the lever 62, as depicted in FIGS. 10 and 11, providing a peeling motion to separate the top liner 10' from the stack of liners 10. The top liner 10' can then be disengaged from the bottom surface 74 and removed from the container 20. In this way, the container 20 provides a convenient storage solution for liners 10 as well as facilitates the separation and dispensing of liners 10 for use.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A container for storing and dispensing respiratory mask liners, the container comprising:
    a housing defining a cavity therein, wherein the housing has a generally planar base and sidewalls extending upwardly from the base, the housing further comprising one or more posts extending upwardly from the base and arranged to receive respiratory mask liners stored in the container;
    a cover arranged to be received on the housing, the cover including an upper face having an opening formed therein; and
    a lever having a first end and a second end, the lever first end pivotally connected to the cover for engaging and dispensing respiratory mask liners stored within the container through the opening.

2. The container of claim 1, wherein the cover includes recessed tracks formed in opposing sides of the opening, the lever first end received by the tracks to provide a pivotal engagement between the lever and the cover.

3. The container of claim 2, wherein the lever first end is slidably engaged with the tracks such that the lever is movable along the tracks to a desired position with respect to the opening.

4. The container of claim 1, wherein the lever second end includes a handle.

5. The container of claim 1, wherein the lever second end includes an engagement member for temporarily adhering to respiratory mask liners stored within the container.

6. The container of claim 5, wherein the engagement member includes an adhesive or textured bottom surface.

7. The container of claim 1, further comprising a lid having a first end and a second end, the lid first end pivotally connected to the cover and arranged to cover the opening.

8. The container of claim 7, wherein the lid is sized to correspond to a shape of the opening and is received within the opening so as to be flush with the cover when the lid is in a closed configuration.

9. The container of claim 7, wherein the lid second end includes a grip member, the grip member including a latch portion arranged to be received in an aperture formed in the cover to secure the lid to the cover when the lid is in a closed configuration.

10. The container of claim 1, wherein the cover includes a tab extending outwardly from a front end thereof.

11. A container for storing and dispensing respiratory mask liners, the container comprising:
    a housing having a generally planar base and sidewalls extending upwardly from the base;
    a cover having an upper face and a rim surrounding the upper face, the rim arranged to be received on the sidewalls of the housing to secure the cover to the housing, the upper face having an opening formed therein, the cover including recessed tracks formed in opposing sides of the opening; and
    a lever having a first end and a second end, the lever first end pivotally connected to the tracks, the lever second end including an engagement member for temporarily adhering to and dispensing respiratory mask liners stored within the container through the opening.

12. The container of claim 11, wherein the lever first end is slidably engaged with the tracks such that the lever is movable along the tracks to a desired position with respect to the opening.

13. The container of claim 11, wherein the lever second end includes a handle.

14. The container of claim 11, wherein the engagement member includes an adhesive or textured bottom surface.

15. The container of claim 11, further comprising a lid having a first end and a second end, the lid first end pivotally connected to the cover and arranged to cover the opening.

16. The container of claim 15, wherein the lid is sized to correspond to a shape of the opening and is received within the opening so as to be flush with the cover when the lid is in a closed configuration.

17. The container of claim 15, wherein the lid second end includes a grip member, the grip member including a latch portion arranged to be received in an aperture formed in the cover to secure the lid to the cover when the lid is in a closed configuration.

18. The container of claim 11, wherein the housing further comprises one or more posts extending upwardly from the base and arranged to receive respiratory mask liners stored in the container.

19. A container for storing and dispensing respiratory mask liners, the container comprising:
    a housing having a generally planar base and sidewalls extending upwardly from the base;
    a cover having an upper face and a rim surrounding the upper face, the rim arranged to be received on the sidewalls of the housing to secure the cover to the housing, the upper face having an opening formed therein, the cover including recessed tracks formed in opposing sides of the opening;
    a lid pivotally connected to the cover and arranged to cover the opening; and
    a lever having a first end and a second end, the lever first end pivotally and slidably connected to the tracks such that the lever is movable along the tracks to a desired position with respect to the opening, the lever second end including an engagement member for temporarily adhering to respiratory mask liners stored within the container and dispensing respiratory mask liners through the opening when the lever is rotated away from the opening.

* * * * *